United States Patent
Hallbäck (10) Patent No.: US 12,064,552 B2
(45) Date of Patent: Aug. 20, 2024

(54) VENTILATION PATTERN FOR HEMODYNAMIC PARAMETER DETERMINATION DURING MECHANICAL VENTILATION

(71) Applicant: MAQUET CRITICAL CARE AB, Solna (SE)

(72) Inventor: Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 875 days.

(21) Appl. No.: 17/250,055

(22) PCT Filed: Jun. 11, 2018

(86) PCT No.: PCT/SE2018/050606
§ 371 (c)(1),
(2) Date: Nov. 13, 2020

(87) PCT Pub. No.: WO2019/240634
PCT Pub. Date: Dec. 19, 2019

(65) Prior Publication Data
US 2021/0220588 A1   Jul. 22, 2021

(51) Int. Cl.
*A61M 16/00*   (2006.01)
*A61M 16/08*   (2006.01)

(52) U.S. Cl.
CPC ... *A61M 16/024* (2017.08); *A61M 2016/0042* (2013.01); *A61M 16/0833* (2014.02);
(Continued)

(58) Field of Classification Search
CPC ............ A61M 16/024; A61M 16/0833; A61M 2016/0042; A61M 2205/3331;
(Continued)

(56) References Cited

U.S. PATENT DOCUMENTS

2002/0174866 A1* 11/2002 Orr ............. A61B 5/029
                                          128/204.22
2015/0217069 A1*  8/2015 Novotni ......... A61M 16/0069
                                          128/204.23

FOREIGN PATENT DOCUMENTS

EP    1579882 A1 *  9/2005  ............. A61B 5/085
WO    2013/141766    9/2013
WO    2017/105304    6/2017

OTHER PUBLICATIONS

Machine Translation of EP-1579882-A1. Accessed from PE2E Search tool on Jan. 2024. (Year: 2005).*

(Continued)

*Primary Examiner* — Kendra D Carter
*Assistant Examiner* — Jaeick Jang
(74) *Attorney, Agent, or Firm* — Fay Kaplun & Marcin, LLP (57) ABSTRACT

A method for changing the effective ventilation of a mechanically ventilated subject to enable or carry out non-invasive determination of hemodynamic parameters is disclosed. The method includes a step of ventilating the subject using a ventilation pattern comprising at least one phase of increased ventilation and at least one phase of decreased ventilation, wherein the phase of decreased ventilation comprises at least one prolonged breath including a respiratory pause (IRP). The respiratory pause is initiated when the lung pressure ($P_{alv}$) of the subject is between a minimum lung pressure and a maximum lung pressure of the subject during the prolonged breath.

15 Claims, 2 Drawing Sheets

(52) U.S. Cl.
CPC . *A61M 2205/3331* (2013.01); *A61M 2205/50* (2013.01); *A61M 2230/432* (2013.01)

(58) Field of Classification Search
CPC ........ A61M 2205/50; A61M 2230/432; A61M 16/12; A61M 2205/502; A61M 16/00; A61B 5/02
See application file for complete search history.

(56) References Cited

OTHER PUBLICATIONS

Gedeon et al., "A new method for noninvasive bedside determination of pulmonary blood flow", Medical & Biological Engineering & Computing, vol. 18, No. 4, Jul. 1, 1980, pp. 411-418.
Gedeon et al., "Pulmonary blood flow (cardiac output) and the effective lung volume determined from a short breath hold using the differential fick method", Journal of Clinical Monitoring and Computing, vol. 17, No. 5, Jan. 1, 2002. pp. 313-321.

* cited by examiner

VENTILATION PATTERN FOR HEMODYNAMIC PARAMETER DETERMINATION DURING MECHANICAL VENTILATION

TECHNICAL FIELD

The present invention relates to a method, a computer program and a breathing apparatus for changing the effective ventilation of a mechanically ventilated subject in order to enable or carry out non-invasive determination of hemodynamic parameters.

BACKGROUND

During mechanical ventilation there is sometimes a desire to actively change the effective ventilation of the patient for diagnostic purposes. For example, a change in effective ventilation may be introduced in order to analyse the response to the change by the respiratory and/or circulatory system of the patient. In this way, important parameters relating to the hemodynamics of the patient can be determined during ongoing ventilation.

The effective ventilation of the patient is typically changed in order to introduce changes in the level of expired CO2, which changes can be used for non-invasive determination of hemodynamic parameters related to, e.g., the effective lung volume (ELV), effective pulmonary blood flow (EPBF), cardiac output (Q) and/or carbon dioxide content of venous blood (CvCO2) of the patient. Monitoring such parameters is important when the cardiovascular stability and/or the lung function of the patient is potentially threatened, e.g. during surgery or ventilation of critically ill patients.

A non-invasive CO2-based method for determination of ELV, Q, EPBF and CvCO2 is disclosed in EP2641536. In order to enable determination of the hemodynamic parameters, the patient is ventilated using a cyclic ventilation pattern wherein each cycle comprises a first number of breaths of increased ventilation and a second number of breaths of decreased ventilation. In one embodiment, the changes in effective ventilation are effectuated by prolonging the inspiratory pause of breaths of decreased ventilation compared to the inspiratory pause of breaths of increased ventilation.

WO2017/105304 discloses another ventilation pattern for enabling determination of hemodynamic parameters, such as ELV, Q, EPBF and CvCO2, e.g., using the method disclosed in EP2641536. The proposed ventilation pattern is adapted to force the level of expired CO2 to assume a substantially steady state following a change in effective ventilation. This is advantageous in that the determination of the physiological parameters can be made using a ventilation pattern that is short in duration while still allowing the parameters to be determined with a high degree of certainty using non-complex algorithms. In accordance with the teachings of EP2641536, changes in effective ventilation may be made by changing the duration of the breaths in the ventilation pattern. WO2017/105304 proposes the effective ventilation to be changed by changing the duration of a pre-inspiratory pause since this has been proved relatively lenient to the perfusion of the patient's lung, and so to provide for reliable determination of Q, EPBF and CvCO2 from breaths of substantially steady state. As well-known in the art, a pre-inspiratory pause is a respiratory pause that is made after expiration and prior to inspiration by the patient, during which pause the pressure is maintained at a level corresponding to a positive end-expiratory pressure (PEEP) of the previous breath. Alternatively, in WO2017/105304, the effective ventilation may be changed by prolonging the duration of an end-inspiratory pause in relation to any end-inspiratory pause of a preceding breath. This may be advantageous compared to changing the duration of a pre-inspiratory pause since the determination of ELV may become more robust and reliable. As also well-known in the art, an end-inspiratory pause is a respiratory pause that is made after inspiration and prior to expiration by the patient, during which pause the pressure is maintained at a level corresponding to an end-inspiratory pressure of the current breath.

However, using a ventilation pattern wherein the effective ventilation of the patient is changed by introducing or changing the duration of pre-inspiratory or end-inspiratory pauses may in certain circumstances be non-optimal. The relatively low lung pressure during pre-inspiratory pauses and the relatively high lung pressure during end-inspiratory pauses could potentially influence the venous return of the ventilated patient. Changes in venous return may, in turn, cause changes in perfusion of the patient's lungs. Varying lung perfusion is a challenge in most methods for non-invasive determination of hemodynamic parameters since these methods are typically based on the assumption that the perfusion remains constant during the period for parameter determination.

Another challenge associated with ventilation patterns comprising pre-inspiratory pauses is the relatively long periods of low lung pressure, potentially increasing the tendency of alveolar deflation, which tendency is most significant if the PEEP is set too low in relation to the pulmonary mechanics of the patient.

Another challenge associated with ventilation patterns comprising end-inspiratory pauses is the increased risk of adversely affecting the hemodynamics of the ventilated patient due to relatively long periods of high airway and thorax pressures.

Consequently, known ways of introducing changes in the effective ventilation of mechanically ventilated patients for determination of hemodynamic parameters such as ELV, Q, EPBF and CvCO2 suffer from certain shortcomings.

SUMMARY

It is an object of the disclosure to present a way of changing the effective ventilation of a mechanically ventilated subject in a lenient manner with a minimum of impact on the pulmonary mechanics and/or the hemodynamics of the patient.

Another object of the disclosure is to present a way of changing the effective ventilation of a mechanically ventilated subject with a minimum of impact on the ongoing ventilatory treatment.

Another object of the disclosure is to present a way of changing the effective ventilation of a mechanically ventilated subject that enables non-invasive determination of at least one hemodynamic parameter with a high degree of certainty.

Yet another object of the disclosure is to present an apparatus or other means for enabling or carrying out non-invasive determination of at least one hemodynamic parameter related to the hemodynamics of a mechanically ventilated subject while at the same time solving or mitigating one or more of the above discussed shortcomings of prior art.

These and other objects are achieved in accordance with the present disclosure by a method, a computer program and a breathing apparatus as defined by the appended claims.

According to an aspect of the disclosure, there is provided a method for changing effective ventilation of a mechanically ventilated subject. The method comprises a step of ventilating the subject using a ventilation pattern comprising at least one phase of increased ventilation and at least one phase of decreased ventilation, wherein the phase of decreased ventilation comprises at least one prolonged breath including a respiratory pause. The respiratory pause is initiated at a point in time when the lung pressure of the subject is at an intermediate pressure level between a minimum and maximum lung pressure of the subject during the prolonged breath.

According to another aspect of the present disclosure, there is provided a method for enabling determination of at least one hemodynamic parameter of a ventilated subject from flow and CO2 measurements obtained during mechanical ventilation of the subject. The method comprises the step of ventilating the subject using a ventilation pattern comprising at least one phase of increased ventilation and at least one phase of decreased ventilation, wherein the phase of decreased ventilation comprises at least one prolonged breath including a respiratory pause. The respiratory pause is initiated when the lung pressure of the subject is at an intermediate pressure level between a minimum and maximum lung pressure of the subject during the prolonged breath. The at least one hemodynamic parameter may be one or more hemodynamic parameters selected from the group consisting of ELV, Q, EPBF and CvCO2.

The minimum lung pressure of a breath typically corresponds to a preset positive end-expiratory pressure (PEEP), and the maximum lung pressure of a breath typically corresponds to an end-inspiratory pressure obtained at the end of inspiration of the prolonged breath. Consequently, the respiratory pause is typically initiated at an intermediate pressure level that is higher than PEEP and lower than the end-inspiratory pressure of the prolonged breath.

The respiratory pause that is initiated at the intermediate pressure level will hereinafter be referred to as an intermediate respiratory pause (IRP).

An advantage of prolonging the breath of decreased ventilation using an IRP instead of a pre-inspiratory pause is that the relatively higher lung pressure during IRP reduces the risk of lung collapse (atelectasis), thus improving patient safety.

An advantage of using an IRP instead of an end-inspiratory pause is that the relatively lower lung pressure during IRP is more lenient and reduces the risk of adversely affecting the hemodynamics of the subject.

Furthermore, by using an IRP instead of a pre-inspiratory pause (where pressure is maintained at PEEP level) or an end-inspiratory pause (where pressure is maintained at an end-inspiratory pressure level), the mean lung pressure of the subject during the prolonged breath will not deviate to the same extent from a mean lung pressure of non-prolonged breaths, i.e. breaths comprising no or a shorter respiratory pause. This, in turn, reduces variations in lung perfusion between prolonged breaths and non-prolonged breaths, which allows hemodynamic parameters, such as Q, EPBF and CvCO2, to be more precisely determined from variations in expired CO2 using known non-invasive methods.

Another advantage of minimising changes in mean lung pressure over time is that the changes in effective ventilation are less prone to adversely affect the overall ventilatory treatment of the subject.

Typically, the lung pressure of the subject is kept at a substantially constant level during the IRP. This means that the intermediate pressure level at which the IRP is initiated is maintained for the duration of the IRP. The intermediate pressure level is typically set to correspond to a mean pressure level of non-prolonged breaths, thereby causing the mean lung pressure of the prolonged breath to correspond to the mean lung pressure of non-prolonged breaths. This has the effect of eliminating or at least further reducing variations in lung perfusion between prolonged breaths of decreased ventilation and non-prolonged breaths of increased ventilation, thus further reducing uncertainty in hemodynamic parameter determination made from CO2 measurements obtained during phases of increased and decreased ventilation.

The IRP may be an intra-inspiratory pause or an intra-expiratory pause, meaning that the pause can be made either within an inspiration phase or within an expiration phase of the prolonged breath. Preferably, the IRP is an intra-inspiratory pause. An advantage of using intra-inspiratory pauses compared to using intra-expiratory pauses is that the introduction of the IRP does not disrupt or interfere with the expiration phase, thereby providing for more reliable determination of hemodynamic parameters determined from measurements of expired CO2 content. Another advantage is that the decrease in ventilation caused by an intra-inspiratory pause will have an immediate impact on the expiration phase of the same breath, meaning that variations in expired CO2 caused by an intra-inspiratory pause can be measured and analysed with a minimum of delay. This improves the response time in methods for hemodynamic parameter determination based on expired CO2 measurements.

The IRP may, in some embodiments, be initiated when an estimated lung pressure of the ventilated subject reaches a threshold value, corresponding to the intermediate pressure level. The lung pressure of the ventilated subject may be estimated from pressure measurements obtained by one or more pressure sensors in the breathing circuit of the ventilator providing mechanical ventilation to the subject, for instance by a proximal pressure sensor obtaining pressure measurements substantially corresponding to the airway pressure of the ventilated subject. The threshold value is preferably set to correspond to a mean lung pressure of non-prolonged breaths, which gives the above described advantages of minimising variations in lung pressure and lung perfusion between prolonged and non-prolonged breaths.

Alternatively, the IRP may be initiated in accordance with a predetermined flow or pressure profile applied to the ventilated subject. For example, the IRP may be initiated in accordance with a parameterized flow profile.

The IRP is typically caused by preventing flow of gas into and out of a breathing circuit through which the subject is connected to the breathing apparatus. Typically, the IRP is performed by the breathing apparatus carrying out an occlusion manoeuvre, e.g. by the closing of an inspiration valve and an expiration valve of the breathing apparatus for the duration of the IRP.

The total number of breaths of increased and decreased ventilation is preferably three or more. This is to enable determination of hemodynamic parameters, such as EPBF or cardiac output, by means of known Fick-based techniques during ventilation of the subject using the proposed ventilation pattern, as will be further described below. The phase of increased ventilation and the phase of decreased ventilation comprises at least one breath each, wherein the at least one breath in the phase of decreased ventilation comprises an IRP in order to decrease a level of ventilation of the subject in relation to the level of ventilation of the subject provided by the at least one breath in the phase of increased ventilation. Typically, the phase of decreased ventilation comprises two or more breaths. In this case, each breath of decreased ventilation may comprise a respective IRP. The IRPs of the breaths of decreased ventilation may have the same durations. However, they may also differ in duration in order to cause a level of CO2 expired in each breath to assume a substantially steady state between breaths within the phase of decreased ventilation. To this end, a first breath and a second breath in the phase of decreased ventilation may comprise a respective IRP, where the duration of the IRP of the first breath is longer than the duration of the IRP of the second breath.

The duration of each IRP may be predetermined and fixed, or it may be continuously or intermittently adapted based on expiratory CO2 measurements.

The method may further comprise a step of non-invasively determining at least one hemodynamic parameter relating to the hemodynamics of the ventilated subject based on flow and CO2 measurements obtained during mechanical ventilation of the subject using the proposed ventilation pattern. For example, the method may comprise a step of non-invasively determining at least one hemodynamic parameter relating to ELV, Q, EPBF and/or CvCO2. Preferably, the method involves determination of at least Q or EPBF of the ventilated subject.

Consequently, according to yet another aspect of the present disclosure, there is provided a method for non-invasively determining at least one hemodynamic parameter of a ventilated subject. The method comprises the step of ventilating the subject using a ventilation pattern comprising at least one phase of increased ventilation and at least one phase of decreased ventilation, wherein the phase of decreased ventilation comprises at least one prolonged breath including a respiratory pause. The respiratory pause is initiated when the lung pressure of the subject is at an intermediate pressure level between a minimum and maximum lung pressure of the subject during the prolonged breath. The method further comprises a step of determining the at least one hemodynamic parameter from flow and CO2 measurements obtained during an analysed sequence of breaths of the ventilation pattern.

The at least one hemodynamic parameter may, for instance, be determined using a non-invasive Fick technique. For example, it may be determined using known CO2-based Fick techniques for cardiac output or EPBF determination. Preferably, the at least one hemodynamic parameter is determined using the method disclosed in EP2641536, where the at least one hemodynamic parameter is determined based on a correlation between parameters derived from the flow and CO2 measurements obtained during the analysed sequence of breaths. In more detail, the at least one hemodynamic parameter may be determined by first determining, for each breath in the sequence of analysed breaths, a first parameter related to the fraction of alveolar CO2 ($F_ACO_2$) of the subject, a second parameter related to the CO2 concentration in alveolar capillaries ($C_ACO_2$) of the subject, and a third parameter ($VTCO_2$) related to CO2 elimination ($VCO_2$) of the subject, from the measured flow and CO2 content. The at least one hemodynamic parameter may then be determined based on a correlation of the first, second and third parameters in the analysed sequence of breaths.

The at least one determined hemodynamic parameter value may be presented to a breathing apparatus operator in order for the operator to take suitable actions. It may also be used as control parameter in automatic feedback control of the breathing apparatus.

According to another aspect of the present disclosure there is provided a breathing apparatus, such as a ventilator or an anaesthesia apparatus, capable of performing the above described method of changing the effective ventilation of a subject in order to enable or carry out non-invasive determination of at least one hemodynamic parameter related to the hemodynamics of the subject from flow and CO2 measurements.

To this end, there is provided a breathing apparatus for changing effective ventilation of a subject connected to the breathing apparatus. The breathing apparatus comprises a control computer, e.g. a control computer, configured to control the operation of the breathing apparatus such that the subject is ventilated using a ventilation pattern comprising at least one phase of increased ventilation and at least one phase of decreased ventilation, wherein the phase of decreased ventilation comprises at least one prolonged breath including a respiratory pause. The control computer is configured to cause the respiratory pause to be initiated at a point in time when the lung pressure of the subject is between a minimum lung pressure and a maximum lung pressure of the subject during the prolonged breath, thereby causing initiation of an IRP.

Typically, the breathing apparatus comprises a pneumatic unit for delivery of pressurised breathing gas to the ventilated subject, the control computer being configured to control the pneumatic unit to deliver breaths of breathing gas to the subject in accordance with said ventilation pattern.

For reasons discussed above, the control computer may be configured to cause the IRP to be initiated at an intermediate pressure level that is higher than a positive end-expiratory pressure (PEEP) level of a previous breath and lower than an end-inspiratory pressure level of the prolonged breath, and preferably at an intermediate pressure level substantially corresponding to a mean lung pressure of the subject during breaths of increased ventilation.

Preferably, the control computer is configured to cause the IRP to be initiated in form of an intra-inspiratory pause within an inspiration phase of the prolonged breath.

The control computer may be configured to cause the phase of decreased ventilation to include at least a second breath comprising an IRP, following said prolonged breath. The control computer may be configured to make the duration of the IRP of the second breath shorter than the duration of the IRP of the prolonged breath in order to cause a level of expired CO2 to assume a substantially steady state within the phase of decreased ventilation.

The breathing apparatus may further be configured to carry out the above described determination of the at least one hemodynamic parameter relating to the hemodynamics of the ventilated subject. To this end, the breathing apparatus may comprise a flow sensor for measuring at least an expiratory flow of expiration gas exhaled by the subject, and a CO2 sensor for measuring the CO2 content of at least the expiration gas exhaled by the subject. The control computer may be configured to determine the at least one hemodynamic parameter from flow and CO2 measurements obtained by said sensors during an analysed sequence of breaths during which the subject is ventilated using said ventilation pattern.

The logic required to enable the breathing apparatus to carry out these steps is preferably implemented by means of software. Thus, according to yet another aspect of the present disclosure there is provided a computer program for changing effective ventilation of a subject connected to a breathing apparatus. The computer program comprises computer readable code which, when executed by a control computer of the breathing apparatus, causes the breathing apparatus to ventilate the subject using a ventilation pattern comprising at least one phase of increased ventilation and at least one phase of decreased ventilation, wherein the phase of decreased ventilation comprises at least one prolonged breath including a respiratory pause. The computer program causes the breathing apparatus to initiate the respiratory pause when the lung pressure of the subject is between a minimum lung pressure and a maximum lung pressure of the subject during the prolonged breath. The computer program may further comprise code segments for causing the breathing apparatus to carry out any steps in the method discussed above.

Installation of such a computer program on existing breathing apparatuses may allow existing breathing apparatuses to carry out the method of the present disclosure without or with a minimum of hardware modification.

More advantageous aspects of the proposed method, breathing apparatus and computer program will be described in the detailed description of embodiments following hereinafter.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DETAILED DESCRIPTION

Figure 1:
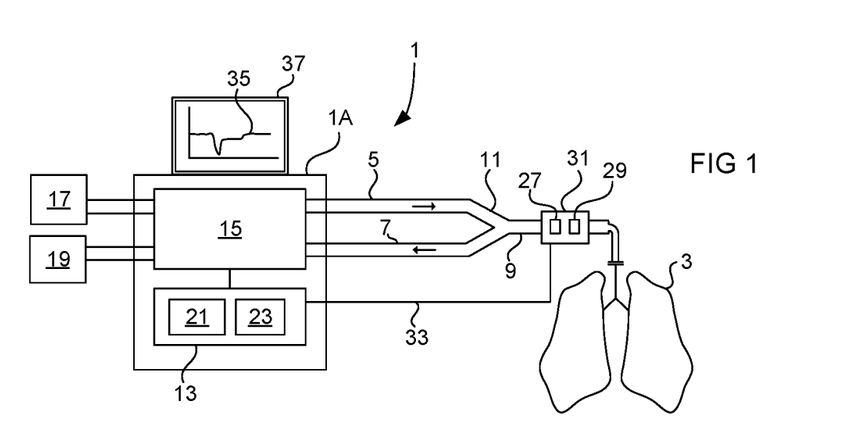
FIG. 1 illustrates a breathing apparatus according to an exemplary embodiment of the disclosure.

FIG. 1 illustrates a breathing apparatus 1 for providing ventilatory treatment to a subject 3 through mechanical ventilation. The breathing apparatus 1 is configured to periodically or intermittently change or alter the effective ventilation of the subject 3 for diagnostic purposes while providing adequate overall ventilation to the subject. In more detail, the breathing apparatus 1 is configured to change the effective ventilation of the subject 3 in order to non-invasively determine one or more parameters related to the hemodynamics of the subject, such as the effective lung volume (ELV), the cardiac output (Q), the effective pulmonary blood flow (EPBF) and/or the carbon dioxide content of venous blood (CvCO2) of the subject 3. Preferably, the breathing apparatus is configured to change the effective ventilation of the subject according to a cyclic ventilation pattern allowing the one or more hemodynamic parameters to be determined continuously.

In the illustrated embodiment, the breathing apparatus 1 is a ventilator for providing ventilatory treatment to the subject 3 (hereinafter referred to as the patient). The ventilator is connected to the patient 3 via an inspiratory line 5 for supplying breathing gas to the patient, and an expiratory line 7 for conveying expiration gas away from the patient. The inspiratory line 5 and the expiratory line 7 are connected to a common line 9, via a so called Y-piece 11, which common line is connected to the patient 3 via a patient connector, such as an endotracheal tube. The inspiratory line 5, the expiratory line 7, the Y-piece 11 and the patient connector form part of a breathing circuit of the breathing apparatus. The breathing circuit is constituted by all gas passages of the breathing apparatus that are in fluid communication with the airways of the patient 3.

The breathing apparatus 1 further comprises a control unit or control computer 13 for controlling the ventilation of the patient 3 based on preset parameters and/or measurements obtained by various sensors of the breathing apparatus. The control computer 13 controls the ventilation of the patient 3 by controlling a pneumatic unit 15 of the breathing apparatus 1, which pneumatic unit 15 is connected at one hand to one or more gas sources 17, 19 and at the other hand to the inspiratory line 5 for regulating a flow and/or pressure of breathing gas delivered to the patient 3. To this end, the pneumatic unit 15 may comprise various gas mixing and regulating means, such as mixing chambers, controllable gas mixing valves and one or more controllable inspiration valves.

The control computer 13 comprises a processing unit 21 and a non-volatile memory 23 storing a computer program which, when executed by the processing unit 21, causes the control computer to control the ventilation of the patient 3 as described hereinafter. Unless stated otherwise, actions and method steps described hereinafter are performed by, or caused by, the control computer 13 upon execution of different code segments of the computer program stored in the memory 23.

The control computer 13 is configured to cause the breathing apparatus 1 to ventilate the patient 3 in accordance with a ventilation pattern that is adapted to enable reliable determination of one or more hemodynamic parameters from measured flow and CO2 content.

The ventilation pattern comprises at least one phase of increased ventilation and at least one phase of decreased ventilation. The phase of increased ventilation comprises at least one breath of increased ventilation and the phase of decreased ventilation comprises at least one breath of decreased ventilation. A breath of increased ventilation is a breath that more efficiently ventilates the lungs of the patient than a breath of decreased ventilation, and vice versa. The purpose of changing the effective ventilation of the patient by providing alternating sequences of breaths of increased ventilation and breaths of decreased ventilation is to cause changes in the level of expired CO2, which changes can be measured and used in the determination of the hemodynamic parameters. Therefore, in this context, a breath of decreased ventilation may also be defined as a breath that causes an increase in the level of expired CO2 compared to a breath of increased ventilation, and vice versa. For reasons discussed in more detail below, the total number of breaths in the phases of increased and decreased ventilation is preferably three or more.

In accordance with the teachings of the present disclosure, the phase of decreased ventilation comprises at least one prolonged breath that includes a respiratory pause. That the phase of decreased ventilation comprises at least one prolonged breath means that that at least one of the breaths of decreased ventilation is prolonged in relation to the breaths of increased ventilation.

The prolongation of the at least one breath of decreased ventilation is achieved by introducing a respiratory pause during the breath, or by prolonging a respiratory pause of the breath in relation to any respiratory pause of the breaths of increased ventilation. The respiratory pause of the prolonged breath is initiated at an intermediate pressure level when the lung pressure of the patient is higher than a minimum lung pressure of the prolonged breath (typically corresponding to a set positive end-expiratory pressure, PEEP, level), and lower than a maximum lung pressure of the prolonged breath (typically corresponding to an end-inspiratory pressure). This means that the respiratory pause is not a pre-inspiratory pause made at a minimum PEEP level, nor an end-inspiratory pause made at a maximum end-inspiratory pressure level of the breath. Instead, the respiratory pause is what is herein referred to as an intermediate respiratory pause (IRP) that is made at an intermediate lung pressure level somewhere between a minimum and maximum lung pressure level of the breathing cycle.

Figure 2:
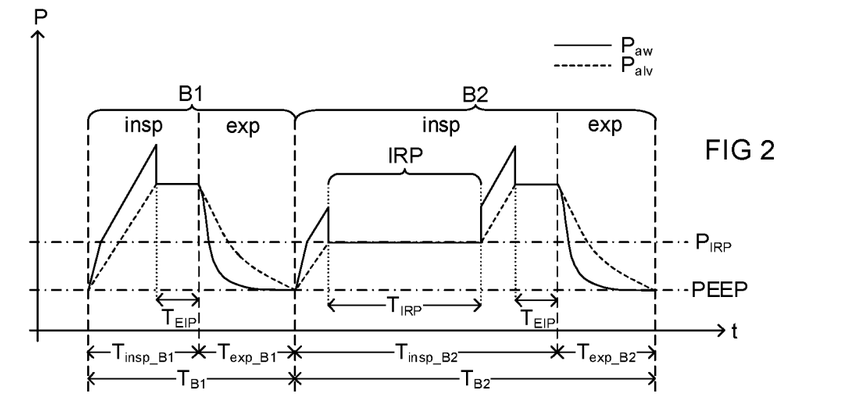
FIG. 2 illustrates parts of a ventilation pattern according to an exemplary embodiment of the disclosure, where the ventilation pattern is generated by a breathing apparatus operated in a volume-controlled mode of operation.

FIG. 2 is a pressure-time diagram illustrating parts of a ventilation pattern according to an exemplary embodiment of the present disclosure. As mentioned above, each phase of increased ventilation typically comprises at least two breaths of increased ventilation and each phase of decreased ventilation typically comprises at least two breaths of decreased ventilation. For illustrative purposes, however, only one breath of increased ventilation and one breath of decreased ventilation are illustrated in FIG. 2.

The continuous graph in the diagram represents the airway pressure ($P_{aw}$) of the ventilated patient, which pressure may be measured, e.g., by a pressure sensor located in the breathing circuit of the breathing apparatus 1. The dashed graph in the diagram represents the lung pressure ($P_{alv}$), sometimes referred to as the alveolar pressure, of the ventilated patient. $P_{alv}$ is closely related to $P_{aw}$ and can be estimated from $P_{aw}$ using known techniques, for example low-pass filtering techniques employing a pneumatic time constant derived from the resistance and compliance of the respiratory system of the patient.

The ventilation pattern in FIG. 2 may be applied to the patient 3 by the breathing apparatus 1 illustrated in FIG. 1 when operated in a type of volume-controlled (VC) mode of operation incorporating IRPs to induce changes in the effective ventilation of the patient.

As illustrated in the drawing, the ventilation pattern comprises a first breath B1 of increased ventilation and a second breath B2 of decreased ventilation. The first breath B1 may, for instance, be the last of breath in a sequence of breaths of increased ventilation, and the second breath B2 may, for instance, be the first breath in a subsequent sequence of breaths of decreased ventilation. The breath B2 of decreased ventilation has a duration $T_{B2}$ that is prolonged in relation to the duration $T_{B1}$ of breath B1 of increased ventilation.

The first breath B1 is a conventional volume-controlled breath in which a desired tidal volume of breathing gas is delivered to the lungs of the patient, typically at constant flow. The delivery of breathing gas to the lungs of the patient causes an increase in lung pressure from a PEEP level of a previous breath (not shown) to a higher end-inspiratory pressure level. The end-inspiratory lung pressure is the maximum lung pressure of the breathing cycle. The inspiration phase of breath B1 is further seen to comprise an end-inspiratory pause during which the end-inspiratory pressure level is maintained for a duration $T_{EIP}$ of the end-inspiratory paus. The end-inspiratory pause may be effectuated by the breathing apparatus through an occlusion manoeuvre, effectively preventing gas from flowing into or out of the breathing circuit. After the end-inspiratory pause, the expiration phase of breath B1 is commenced, e.g. through removal of the occlusion. During expiration, the lung pressure of the patient drops from the maximum end-inspiratory pressure level towards the PEEP level. The PEEP level defines a minimum lung pressure of the breathing cycle.

When the expiration phase of the first breath B1 is over, a flow of breathing gas is once again delivered to the patient to initiate the inspiration phase of the subsequent and prolonged breath B2. As a consequence of breathing gas delivery, the lung pressure of the patient rises from the PEEP level of the previous breath B1 towards and end-inspiratory pressure level of breath B2. However, before the end-inspiratory pressure level is reached, i.e. before the entire tidal volume of breathing gas has been delivered to the patient in breath B2, an IRP is initiated by the breathing apparatus at an intermediate lung pressure level ($P_{IRP}$). After the IRP, the inspiration phase of B2 is resumed and completed in accordance with the inspiration phase of the breath B1 of increased ventilation. In a VC mode, this means that the remains of the preset tidal volume are delivered to the patient after the IRP. An end-inspiratory pause corresponding to the end-inspiratory pause in breath B1 of increased ventilation is then made before the expiration is commenced. The expiration phase of the prolonged breath B2 is identical to the expiration phase of breath B1 of increased ventilation.

The IRP is characterised mainly by the duration of the IRP ($T_{IRP}$) and the intermediate pressure level $P_{IRP}$ at which it is initiated. The IRP may be effectuated by the breathing apparatus by carrying out an automatic occlusion manoeuvre effectively preventing flow into and out of the breathing circuit for the duration $T_{IRP}$ of the IRP.

The duration $T_{IRP}$ of the IRP is typically predetermined and set to provide for a substantial increase in the level of expired CO2 content during the breath B2 of decreased ventilation compared to the level of expired CO2 content during the breath B1 of increased ventilation. Typically, the duration $T_{IRP}$ of the IRP is of the same order of magnitude as the duration $T_{B1}$ of the entire breath B1 of increased ventilation. Typically, for adult patients, both the duration of the IRP and the duration of the breath B1 of increased ventilation are about 4 seconds. In this case, the duration of the entire prolonged breath B2 is typically about 8 seconds. For children and neonates, the duration of the IRP and the duration of the breaths should be substantially shorter. Typically, all breaths of increased ventilation in the ventilation pattern have substantially the same length or duration. Each of the breaths of decreased ventilation in the ventilation pattern may, as discussed in more detail below, comprise a respective IRP. The duration of the IRP may be the same for all breaths of decreased ventilation, or it may vary in order to obtain a substantially steady state of expired CO2 during the phase of decreased ventilation, as also discussed in more detail below.

The mean lung pressure $P_{alv}$ of the patient during the IRP should be in between the minimum and maximum lung pressure level of the breath in order for the proposed ventilation pattern to reduce variations in lung perfusion compared to ventilation patterns employing pre-inspiratory pauses or end-inspiratory pauses. Preferably, to minimise variations in lung perfusion, the mean lung pressure of the patient during the IRP should correspond substantially to the mean lung pressure of the patient during breaths of increased ventilation. Typically, the lung pressure of the patient remains substantially constant during the IRP, which means that the intermediate pressure level $P_{IRP}$ at which the IRP is initiated should be in between the PEEP level and the end-inspiratory pressure of the prolonged breath, and should preferably correspond substantially to a mean lung pressure of the patient during breaths of increased ventilation.

The value of $P_{IRP}$ may be fixed and predetermined, or it may be variable and dynamically calculated from pressure measurements obtained during previous breaths, for instance as the mean lung pressure of previous breaths of increased ventilation.

In one exemplary embodiment, $P_{IRP}$ may serve as a trigger value for triggering the IRP based on the estimated lung pressure of the patient. This means that the starting point in time for the IRP is not predetermined but dependent on the current lung pressure of the ventilated patient. When the estimated lung pressure reaches $P_{IRP}$, the breathing apparatus initiates the IRP and prevents respiration by the patient for the duration $T_{IRP}$ of the IRP. As mentioned before, the lung pressure may be readily estimated by the breathing apparatus, e.g., from measured airway pressure. This principle for triggering of the IRP is applicable in both VC mode and pressure-controlled (PC) operation mode of the breathing apparatus 1.

In another exemplary embodiment, the patient may be ventilated in accordance with a predetermined pressure profile (in PC mode) or a predetermined flow profile (in VC mode), where the point in time for initiation of the IRP is predetermined. Consequently, in this scenario, initiation of the IRP is time triggered and independent of the current lung pressure of the patient. Preferably, the flow or pressure profile is parameterized to cause initiation of the IRP at a point in time where the lung pressure of the patient can be assumed to correspond substantially to a mean lung pressure of the patient during breaths of increased ventilation.

An example of a parameterized flow profile that could be applied to a patient ventilated in VC mode during an inspiration phase of a prolonged breath of decreased ventilation, such as the breath B2 in FIG. 2, is given by:

$$\text{Flow} = \emptyset_1 \text{ for to } t_0 \leq t < t_0 + t_1$$

$$\text{Flow} = 0 \text{ for } t_0 + t_1 \leq t < t_0 + t_1 + T_{IRP}$$

$$\text{Flow} = \emptyset_1 \text{ for } t_0 + t_1 + T_{IRP} \leq t < t_0 + T_{insp} - T_{EIP}$$

$$\text{Flow} = 0 \text{ for } t_0 + T_{insp} - T_{EIP} \leq t \leq t_0 + T_{insp}$$

where $\emptyset_1$ is a constant flow of the VC mode ventilation, to is the start time of the inspiration phase of the prolonged breath, $T_{IRP}$ is the duration of the IRP, $T_{insp}$ is the duration of the inspiration phase of the prolonged breath, and $T_{EIP}$ is the set duration of the end-inspiratory paus. The time $t_1$ may be determined by the relationship $$t_1 \cdot \emptyset_1 = (P_{IRP} - \text{PEEP}) \cdot C_{dyn},$$

where $P_{IRP}$ is a desired lung pressure of the patient at initiation of the IRP, PEEP is the positive end-expiratory pressure of the preceding breath (corresponding to the pre-inspiratory pressure of the prolonged breath), and $C_{dyn}$ is an estimated dynamic compliance of the respiratory system of the patient, which compliance may be estimated from flow and pressure measurements using principles well known in the art.

Correspondingly, the flow profile of an inspiratory phase of a non-prolonged breath of increased ventilation, such as the breath B1 in FIG. 2, could be parameterized in accordance with:

$$\text{Flow} = \emptyset_1 \text{ for } t_0 \leq t < t_0 + T_{insp} - T_{EIP}$$

$$\text{Flow} = 0 \text{ for } t_0 + T_{insp} - T_{EIP} \leq t \leq t_0 + T_{insp}$$

Figure 3:
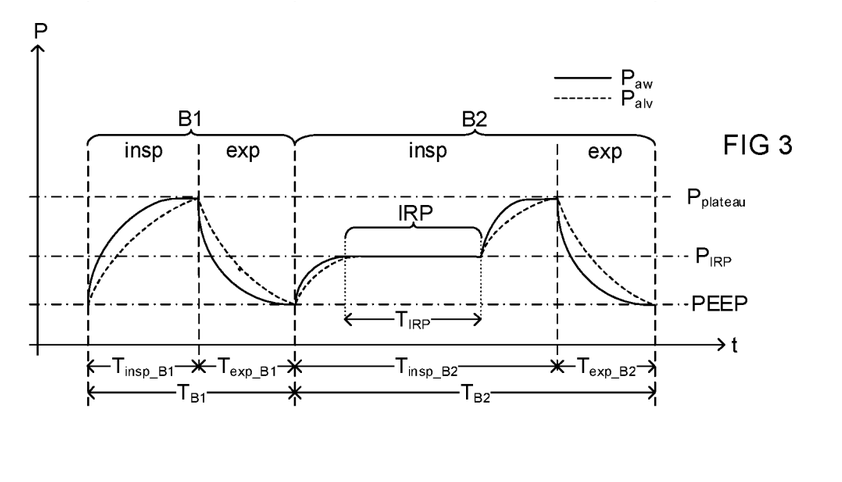
FIG. 3 illustrates parts of a ventilation pattern according to another exemplary embodiment of the disclosure, where the ventilation pattern is generated by a breathing apparatus operated in a pressure-controlled mode of operation.

FIG. 3 is a pressure-time diagram illustrating parts of a ventilation pattern according to another exemplary embodiment of the present disclosure. For illustrative purposes, only one breath of increased ventilation and one breath of decreased ventilation are illustrated. Like in FIG. 2, the continuous graph represents airway pressure $P_{aw}$ and the dashed graph represents lung pressure $P_{alv}$.

The ventilation pattern in FIG. 3 may be applied to the patient 3 by the breathing apparatus 1 illustrated in FIG. 1 when operated in a type of pressure-controlled (PC) mode of operation incorporating IRPs to induce changes in the effective ventilation of the patient.

As illustrated in the drawing, the ventilation pattern comprises a first breath B1 of increased ventilation and a second breath B2 of decreased ventilation. The first breath B1 may, for instance, be the last breath in a sequence of breaths of increased ventilation, and the second breath B2 may, for instance, be the first breath in a subsequent sequence of breaths of decreased ventilation. The breath B2 of decreased ventilation has a duration $T_{B2}$ that is prolonged in relation to the duration $T_{B1}$ of breath B1 of increased ventilation.

The first breath B1 is a conventional pressure-controlled breath in which the pressure applied to the airways of the patient is increased from a PEEP pressure of a preceding breath to a set plateau pressure $P_{plateau}$. The lung pressure $P_{alv}$ of the patient is seen to follow the airway pressure $P_{aw}$ with a slight delay. The plateau pressure is then maintained for the remains of a set duration $T_{insp\_B1}$ of the inspiration phase. Upon expiry of the duration of the inspiration phase, the expiration phase of breath B1 is commenced by reducing the applied pressure to the PEEP level.

When the expiration phase of breath B1 is over, the inspiration phase of the prolonged breath B2 is commenced by raising the applied pressure from the PEEP level of B1 (corresponding to a pre-inspiratory pressure of B2) to an intermediate pressure level $P_{IRP}$ that is higher than the PEEP level and lower than the plateau pressure $P_{plateau}$. By maintaining the applied pressure at the intermediate pressure level for a certain period of time, an IRP in accordance with the principles of the present disclosure is introduced, causing a decrease in the effective ventilation of the patient resulting in an increase in the level of expired $CO_2$. For reasons discussed above, $P_{IRP}$ should preferably correspond substantially to the mean lung pressure of the patient during phases of increased ventilation. After the period of time during which the applied pressure has been maintained at $P_{IRP}$, corresponding to a duration $T_{IRP}$ of the IRP, the pressure is further increased to the plateau level $P_{plateau}$ in order to resume and complete the inspiration phase of the prolonged breath B2. The plateau pressure is maintained for the remains of a set duration $T_{insp\_B2}$ of the inspiration phase, whereafter expiration is initiated by lowering the applied pressure from the plateau pressure level to the PEEP level. The expiration phase of the prolonged breath B2 is identical to the expiration phase of breath B1 of increased ventilation.

It should be noted that whereas the IRP in FIG. 3 has been described as an intra-inspiratory pause it may as well, depending on the definitions of the inspiratory and expiratory phases, be regarded as a pre-inspiratory pause that is made prior to inspiration, at an elevated PEEP pressure. When regarded as an intra-inspiratory pause, the breathing apparatus 1 can be said to operate in a mode of inspiratory bi-level airway pressure regulation as the airway pressure during inspiration is first regulated towards the intermediate pressure level $P_{IRP}$, and then towards the final plateau pressure level $P_{plateau}$. When regarded as a pre-inspiratory pause, the breathing apparatus 1 can be said to operate in a mode of expiratory bi-level PEEP regulation as the PEEP level during a first part of expiration is maintained at a pressure level which may be regarded as a first and normal (non-elevated) PEEP level, and then, during a final part of expiration, at a pressure level which may be regarded as a second and elevated PEEP level. In this scenario, the intermediate pressure $P_{IRP}$ at which the IRP is initiated is higher than the normal PEEP and lower than the plateau pressure $P_{plateau}$. In any circumstances, no matter the sometimes conflicting definitions of ventilation modes and respiration phases, the IRP of the present disclosure is a respiratory pause that is initiated at an intermediate pressure $P_{IRP}$ that is higher than a minimum lung pressure of the current breath, and lower than a maximum lung pressure of the current breath.

In the above examples, the IRP is made during an inspiration phase of a breath and can thus be said to be an inspiratory IRP. However, it should be appreciated that the IRP may as well be an expiratory IRP that is made during an expiratory phase of a breath. The above described principles of initiating an IRP at an intermediate pressure level are applicable also within expiratory phases, both in VC mode and PC mode. Just like inspiratory IRPs, expiratory IRPs may solve or mitigate the problem of varying lung perfusion during changes in effective ventilation. However, inspiratory IRPs may be advantageous compared to expiratory IRPs in that expiratory IRPs may jeopardize reliability and certainty in expiratory CO2 measurements. The expiratory phase should preferably be identical between breaths of increased and decreased ventilation.

Figure 4:
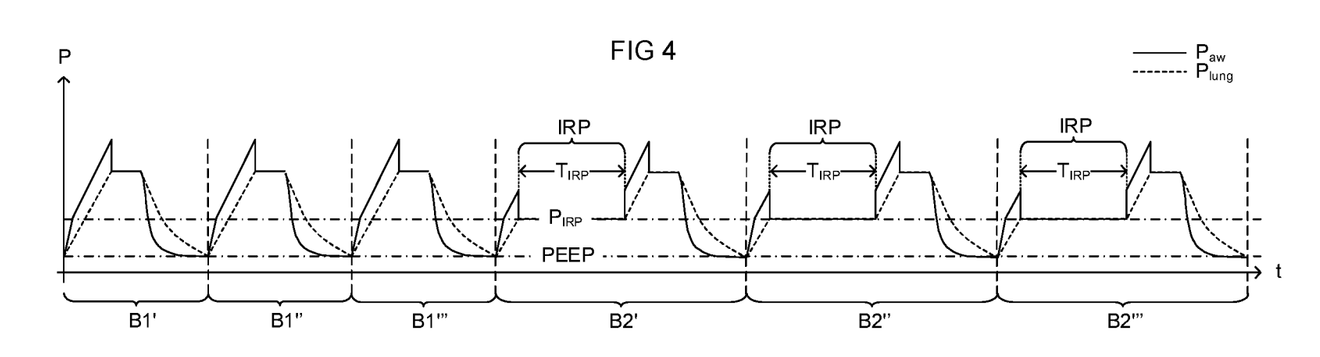
FIG. 4 illustrates a cycle of a cyclic ventilation pattern according to an exemplary embodiment of the disclosure.

FIG. 4 illustrates an exemplary ventilation pattern wherein each phase of increased ventilation comprises three breaths B1', B1'', B1''', each identical to the breath B1 in FIG. 2, and each phase of decreased ventilation comprises three breaths B2', B2'', B2''', each identical to the breath B2 in FIG. 2. This is an example of a ventilation pattern that enables non-invasive determination of one or more parameters related to the hemodynamics of the ventilated subject, such as the ELV, Q, EPBF and/or CvCO2. The ventilation pattern may be a cyclic ventilation pattern comprising alternating phases of decreased and increased ventilation to enable continuous monitoring of the hemodynamics of the ventilated subject. This means that the phase of decreased ventilation is immediately followed by a new phase of increased ventilation, which, in turn, is immediately followed by a new phase of decreased ventilation, and so on. The relatively short cycles of the ventilation pattern provides for quick response time in parameter determination.

The determination of the one or more hemodynamic parameters is preferably made from flow and CO2 measurements using a non-invasive Fick technique. There are many Fick-based methods for non-invasive determination of hemodynamic parameters and many of them may be used with no or a minimum of modification in order to calculate hemodynamic parameters such as Q and EPBF from measurements obtain during mechanical ventilation of a patient using the proposed ventilation pattern.

The determination of the hemodynamic parameters may be made by the breathing apparatus itself or it may be made by external units, such as an external computer or a monitoring system configured to obtain flow and CO2 measurements related to the ongoing ventilation of the patient.

With reference again made to FIG. 1, the breathing apparatus 1 may, in one exemplary embodiment, comprise at least one flow sensor 27 for measuring at least an expiratory flow of expiration gas exhaled by the patient 3, and at least one CO2 sensor 29 for measuring the CO2 content of at least the expiration gas exhaled by the patient. The control computer 13 may be configured to determine the at least one hemodynamic parameter from flow and CO2 measurements obtained during an analysed sequence of breaths during which the patient is ventilated using the proposed ventilation pattern. Preferably, the flow and CO2 sensors 27, 29 are configured to measure also inspiratory flow and CO2 content which, in some circumstances, may be advantageously used together with expiratory flow and CO2 measurements in the determination of hemodynamic parameters.

In the illustrated embodiment, the flow sensor 27 and the CO2 sensor 29 form parts of a capnograph 31 configured for volumetric capnography measurements. The capnograph 31 is arranged in the proximity of the airways opening of the patient 3, namely in the common line 9 of the breathing circuit in which it is exposed to all gas exhaled and inhaled by the patient 3. The capnograph 31 is connected to the breathing apparatus 1 via a wired or wireless connection 33, and configured to transmit the flow and CO2 measurements to the ventilator for further processing by the processing unit 21 of the breathing apparatus. The breathing apparatus 1 is preferably configured to generate a volumetric capnogram 35 from the flow and CO2 measurements received from the capnograph 31, and, additionally, to display the volumetric capnogram 35 on a display 37 of the ventilator.

The control computer 13 of the breathing apparatus 1 may be configured to determine the at least one hemodynamic parameter based on flow and CO2 measurements using the following capnodynamic equation for a single-chamber lung model, which describes how the fraction of alveolar carbon dioxide ($F_A CO2$) varies from one breath to another:

$$ELV \cdot (F_A CO2^n - F_A CO2^{n-1}) = \Delta t^n \cdot EPBF \cdot (CvCO2 - C_A CO2^n) - VTCO2^n \quad \text{(eq. 1)}$$

where ELV is the effective lung volume for CO2 storage at end of expiration, $F_A CO2^n$ is the alveolar CO2 fraction in the lung at end of expiration n, $\Delta t^n$ is the duration of breath n, EPBF is the effective pulmonary blood flow, CvCO2 is the CO2 concentration in mixed venous blood (volume of CO2 gas per volume blood), $C_A CO2^n$ is the CO2 concentration in alveolar capillaries during breath n, and $VTCO2^n$ is the tidal elimination of CO2 in breath n.

$F_A CO2^n$ may be measured by the CO2 sensor 29 while $C_A CO2^n$ and VTCO2 may be directly calculated from $F_A CO2^n$, the tidal volume of breath n (VT"), and a known deadspace volume, as well known in the art, leaving EPBF, CvCO2 and ELV as unknown physiological parameters to be determined.

Equation 1 is analogous to equation 1 in EP2641536 by the same applicant, disclosing a non-invasive and continuous method for simultaneous determination of ELV, cardiac output and CvCO2. The only difference between the equations is that equation 1 in EP2641536 uses the quantities CaCO2 (CO2 concentration or content per volume unit in arterial blood) and Q (cardiac output) whereas equation 1 above uses the quantities $C_A CO2$ and EPBF. As well known in the art, EPBF corresponds to cardiac output minus the intra-pulmonary shunt, and $C_A CO2$ relates to CaCO2 in accordance with the equation: $C_A CO2 = CaCO2 - (CvCO2 - CaCO2) \cdot Qs/EPBF$, where Qs is the shunt flow and CvCO2 is the CO2 concentration in the shunt flow (corresponding to the CO2 concentration in venous blood). EP2641536 and its US counterpart, U.S. Patent Application Publication No. US 2013/0253359 A1 are incorporated herein by reference in their entirety.

The control computer 13 of the breathing apparatus 1 may be configured to use the method disclosed in EP2641536 to determine the parameter triplet {ELV, EPBF, CvCO2} from an analysed sequence of breaths, based on the correlation between the directly measureable or derivable parameters $\Delta F_A CO2$ ($=F_A CO2^n - F_A CO2^{n-1}$), $C_A CO2$ and VTCO2 in said analysed sequence of breaths. Likewise, the control computer 13 may be configured to use the method disclosed in EP2641536 to determine the parameter triplet {ELV, Q, CvCO2} from an analysed sequence of breaths, based on the correlation between the directly measureable or derivable parameters $\Delta F_A CO2$ ($=F_A CO2^n - F_A CO2^{n-1}$), $CaCO2$ and VTCO2 in said analysed sequence of breaths.

Introducing an index 'n' indicating the number of the breath in the analysed sequence of breaths, and rearranging equation 1 such that the unknown parameters are gathered on the left-hand side of the equation yields:

$$ELV \cdot \Delta F_A CO_2^n - EPBF \cdot CvCO_2 \cdot \Delta t^n + EPBF \cdot C_A CO2^n \cdot \Delta t^n = -VTCO_2^n \quad \text{(eq. 2)}$$

Writing this equation in matrix form for the breaths n=1, 2, . . . ,N in the analysed sequence of breaths yields:

$$\begin{bmatrix} \Delta F_A CO_2^1 & -\Delta t^1 & C_A CO_2^1 \cdot \Delta t^1 \\ \vdots & \vdots & \vdots \\ \Delta F_A CO_2^n & -\Delta t^n & C_A CO_2^n \cdot \Delta t^n \\ \vdots & \vdots & \vdots \\ \Delta F_A CO_2^N & -\Delta t^N & C_A CO_2^N \cdot \Delta t^N \end{bmatrix} \cdot \begin{bmatrix} ELV \\ EPBF \cdot CvCO_2 \\ EPBF \end{bmatrix} = \begin{bmatrix} -VTCO_2^1 \\ \vdots \\ -VTCO_2^n \\ \vdots \\ -VTCO_2^N \end{bmatrix} \quad \text{(eq. 3)}$$

When the analysed sequence of breaths N comprises more than three breaths (i.e when N>3), this becomes an overdetermined system of equations and the unknown parameter triplet {ELV, EPBF·CvCO$_2$, EPBF} and hence the physiological parameters ELV, EPBF, and CvCO$_2$ can be determined by finding an approximate solution to the overdetermined system of equation. As well known in the art, the approximate solution to an overdetermined system of equations can be calculated in different ways, e.g. using the method of least squares. The solution to the overdetermined system of equations will depend on the correlation of the parameters $\Delta F_A CO2$, $C_A CO2$ and VTCO2 in the respiratory cycles of the analyses sequence of respiratory cycles.

This system of equations (eq. 3) may be rewritten as $A \cdot x_A = a$, where $$A = \begin{bmatrix} \Delta F_A CO_2^1 & -\Delta t^1 & C_A CO_2^1 \cdot \Delta t^1 \\ \vdots & \vdots & \vdots \\ \Delta F_A CO_2^n & -\Delta t^n & C_A CO_2^n \cdot \Delta t^n \\ \vdots & \vdots & \vdots \\ \Delta F_A CO_2^N & -\Delta t^N & C_A CO_2^N \cdot \Delta t^N \end{bmatrix},$$

$$X_A = \begin{bmatrix} ELV \\ EPBF \cdot CvCO_2 \\ EPBF \end{bmatrix}, \text{ and } a = \begin{bmatrix} -VTCO_2^1 \\ \vdots \\ -VTCO_2^n \\ \vdots \\ -VTCO_2^N \end{bmatrix}$$

The control computer 13 of the breathing apparatus 1 may for example be configured to calculate an approximate solution for the parameter triplet {ELV, EPBF·CvCO$_2$, EBBF} by minimizing the error $|A \cdot x_A - a|$. Using the method of least squares, the solution may be calculated as:

$$x_A = (A^T \cdot A)^{-1} \cdot A^T \cdot a \quad \text{(eq. 4)}$$

Consequently, the control computer 13 may determine approximate values of ELV, EPBF, CvCO2, and Q from flow and CO2 measurements obtained for an analysed sequence of breaths during which the patient 3 is ventilated using the proposed ventilation pattern causing the level of expired CO2 to vary during the analysed sequence of breaths while improving parameter determination by minimizing variations in lung perfusion during the measurement period. For continuous monitoring of ELV, EPBF, Q and/or CvCO2, the ventilation pattern is preferably a cyclic ventilation pattern and the parameters are preferably determined by the control computer 13 on a breath-by-breath basis. Preferably but not necessarily, the number of breaths in said analysed sequence of breaths corresponds to the number of breaths in each cycle of the cyclic ventilation pattern.

The ventilation pattern should preferably be adapted to provide for a desired overall ventilation of the subject. Therefore, the breaths of increased ventilation and the breaths of decreased ventilation may be adapted to provide for a desired mean ventilation of the patient, e.g. in terms of minute volume and mean airway pressure.

Preferably, the breaths of increased ventilation are hyperventilated breaths and the breaths of decreased ventilation are hypoventilated breaths. Thereby, the total ventilation over time can be made to correspond to a desired baseline ventilation of the subject. In this regard it should be emphasized that phases of increased and decreased ventilation should not be construed as being limited to phases of ventilation that are increased and decreased in relation to baseline (normal) ventilation. Instead, it should be understood that in the context of this application, a phase of decreased ventilation is a phase in which ventilation is decreased compared to a phase of increased ventilation, and vice versa. Thus, it should be realized that embodiments wherein the level of ventilation in the phase of increased ventilation or the level of ventilation in the phase of decreased ventilation corresponds to a baseline level of ventilation are also encompassed by the present disclosure.

The ventilation pattern may further be adapted to employ the technique of forced steady state, as described in more detail in WO2017/105304, which is incorporated herein by reference. This is advantageous in that the determination of the hemodynamic parameters can be made using a ventilation pattern that is short in duration while still allowing the parameters to be determined with a high degree of certainty using non-complex algorithms.

To this end, each phase of decreased ventilation may comprise at least a first breath for generating a substantial change in the level of CO2 expired by the patient 3, and at least a second breath, following the at least first breath, for causing the level of expired CO2 to assume a substantially steady state level within the phase of decreased ventilation, i.e. during at least two breaths in said phase of decreased ventilation. Likewise, each phase of increased ventilation may comprise at least a first breath for generating a substantial and opposite change in the level of CO2 expired by the patient 3, and at least a second breath, following the at least first breath, for causing the level of expired CO2 to assume a new substantially steady state level within the phase of increased ventilation (i.e. during at least two breaths in the phase of increased ventilation). In WO2017/105304, the substantial change in the level of expired CO2 is caused by changing the duration and/or volume of the at least one first breath with respect to a preceding breath, and the level of expired CO2 is caused to assume a steady state in the phase of decreased and/or increased ventilation by changing the duration and/or volume of the at least one second breath with respect to the duration and/or volume of the at least one first breath.

In accordance with the principles of the present disclosure, the control computer 13 of the breathing apparatus in FIG. 1 may be configured to cause any or both of the substantial change in the level of CO2 and the subsequent change for causing the level of CO2 to reach a substantially steady state within the phase of decreased and/or increased ventilation by introducing, removing or altering the duration of an IRP.

For example, a substantial increase in expired CO2 may be caused through the introduction of an IRP or the prolongation of an IRP in relation to any IRP of a preceding breath. This corresponds to the scenario illustrated in FIG. 2 where the transition from a phase of increased ventilation to a phase of decreased ventilation is initiated by introducing an IRP into breath B2. Likewise, a substantial decrease in expired CO2 may be caused through the removal of an IRP or, potentially, even the shortening of an IRP in relation to any IRP of a preceding breath.

The substantially steady state within the respective phases of decreased and increased ventilation may also be caused by introducing, removing or altering the duration of an IRP.

For example, a substantially steady state within a phase of decreased ventilation may be reached by shortening the IRP of a second breath of decreased ventilation in relation to the IRP of a first breath of decreased ventilation. Likewise, a substantially steady state within a phase of increased ventilation may be reached by introducing a short IRP into a second breath of increased ventilation, following a first breath of increased ventilation with no IRP.

Figure 5:
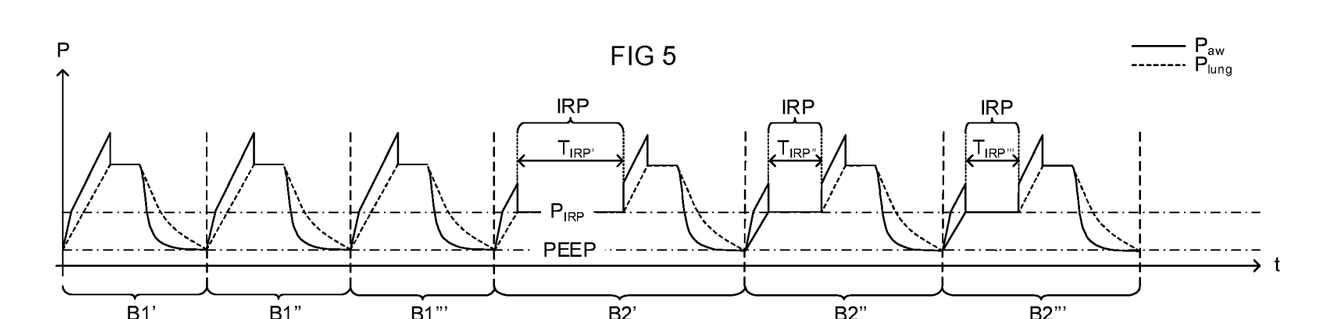
FIG. 5 illustrates a cycle of a cyclic ventilation pattern according to another exemplary embodiment of the disclosure.

FIG. 5 illustrates an exemplary ventilation pattern employing the forced steady-state technique by being adapted to cause the level of expired CO2 to reach a substantially steady state within the phase of decreased ventilation. In accordance with the exemplary ventilation pattern in FIG. 4, the ventilation pattern in FIG. 5 includes a phase of increased ventilation comprising three breaths B1', B1'', B1''' of increased ventilation, and a phase of decreased ventilation comprising three breaths B2', B2'', B2''' of decreased ventilation. The breaths B1', B1'', B1''' of increased ventilation are identical to the breaths of increased ventilation in FIG. 4. The breaths of decreased ventilation, B2', B2'', B2''', however, differ from the breaths of decreased ventilation in FIG. 4 in that the duration of the IRP is not the same for all breaths. The first breath B2' of decreased ventilation is seen to comprise a relatively long IRP (having a duration $T_{IRP'}$) in order to cause a substantial change in the level of expired CO2 compared to the level of expired CO2 in the last breath B1''' of increased ventilation. In the second breath B2'' of decreased ventilation, the duration $T_{IRP''}$ of the IRP is made substantially shorter than the duration $T_{IRP'}$ of the IRP of the first breath B2' of decreased ventilation. The IRP of the second breath B2'' is shortened in order to prevent further increase in the level of expired CO2 and force the level of expired CO2 during the second breath B2'' of decreased ventilation to correspond substantially to the level of expired CO2 during the first breath B2' of decreased ventilation. The third breath B2''' of decreased ventilation may comprise an IRP having a duration $T_{IRP'''}$ which may correspond to the duration $T_{IRP''}$ of the IRP of the second breath B2'', or which may differ from any or both of the durations of the IRPs of the first breath B2' and the second breath B2''. Preferably, the duration $T_{IRP'''}$ of the IRP of the third breath B2''' of decreased ventilation is adapted to maintain the level of expired CO2 at the substantially constant level obtained during the first two breaths B2', B2'' of decreased ventilation.

That the level of expired CO2 assumes a substantially steady state during two breaths herein means that a measure of expired CO2 obtained during a first breath is substantially equal to a corresponding measure of expired CO2 obtained during a second breath. Said measure of expired CO2 may be any measure indicative of alveolar CO2 of the ventilated patient 3, e.g. a measure of the fraction of alveolar CO2 ($F_ACO2$) or a measure of the partial pressure of alveolar CO2 ($P_ACO2$), including but not limited to end-tidal fraction of alveolar CO2 ($F_{et}CO2$) and end-tidal partial pressure of CO2 ($P_{et}CO2$).

The at least two breaths of the same phase of decreased or increased ventilation during which the level of expired CO2 assumes a substantially steady state may or may not be consecutive breaths. If the second breath B2'' of decreased ventilation is or cannot be properly adapted to make the level of CO2 expired during the second breath correspond to the level of CO2 expired during the first breath B2' of decreased ventilation, the duration $T_{IRP'''}$ of the third breath B2''' of decreased ventilation may be adapted to make the level of CO2 expired during the third breath B2''' correspond to the level of CO2 expired during any of the first breath B2' or the second breath B2'' of decreased ventilation.

It should be noted that the exemplary ventilation pattern illustrated in FIG. 5 is adapted for forced steady state only within phases of decreased ventilation. Instead or in addition, it could be adapted for forced steady state within phases of increased ventilation. In certain circumstances, it may be possible to obtain a sufficient change in the level of expired CO2 between phases of increased and decreased ventilation while still obtaining substantially steady states of expired CO2 in both phases of increased and decreased ventilation by no other means than introduction, removal and/or alteration of the duration of IRPs. However, other ways of changing the duration and/or volume of breaths of increased ventilation may be required in order to reach a substantially steady state in the level of expired CO2 within phases of increased ventilation. For example, it may be advantageous to use the proposed principle of altering the durations of IRPs to reach steady state within phases of decreased ventilation, while altering the tidal volume of breaths of increased ventilation to reach steady state also within phases of increased ventilation. As suggested in WO2017/105304 (see FIG. 3A and the description thereof), steady state within phases of increased ventilation may, for example, be obtained by making the tidal volume of the first breath of increased ventilation bigger than the tidal volumes of subsequent breaths of increased ventilation. Notably, this would increase the mean lung pressure of the patient during phases of increased ventilation, which should be accounted for in the selection of suitable intermediate pressure level $P_{IRP}$ for the IRPs in breaths of decreased ventilation.

Consequently, to allow EPBF, Q and CvCO2 to be determined independently of ELV, the breathing apparatus 1 in FIG. 1 may be configured to ventilate the patient 3 using a ventilation pattern employing the above described technique of forced steady state, such as the ventilation pattern illustrated in FIG. 5. In this case, the control computer 13 may be configured to determine EPBF, Q and/or CvCO2 only from breaths during which the level of expired CO2 assumes a substantially steady state, or to determine EPBF, Q and/or CvCO2 from a sequence of breaths in which breaths of substantially steady state are weighted more heavily than breaths of non-steady state, as described in more detail in WO2017/105304. Once EPBF, Q and/or CvCO2 has been determined, the control computer 13 may determine ELV only from transient breaths in said sequence of analysed breaths (i.e., from breaths having different levels of expired CO2 content), or from a sequence of breaths in which transient breaths are weighted more heavily than breaths of steady state, preferably using the determined values of EPBF, Q and/or CvCO2.

The ventilation pattern described herein may be an adaptive ventilation pattern that is automatically adapted based on measured parameters indicative of the response by the patient to the currently applied ventilation pattern. For example, the control computer 13 of the breathing apparatus 1 may be configured to use a measure of expired CO2, e.g. measured by the CO2 sensor 29, as control parameter for feedback control of the duration of IRPs in the breaths of the ventilation pattern. Thus, the control computer 13 may be configured to use expired CO2 for feedback control of the duration of the IRPs in order to achieve a desired change in the level of expired CO2 in the transition between phases of increased and decreased ventilation, and/or to cause the level of expired CO2 to assume a substantially steady state within the phase of increased and/or decreased ventilation. For example, with reference again made to FIG. 5, the control computer 13 may be configured to compare the level of expired CO2 in the first breath B2' of decreased ventilation with the level of expired CO2 in the second and subsequent breath B2" of decreased ventilation, and, if the level of expired CO2 in the second breath deviates from the level of expired CO2 in the first breath by more than a predetermined amount (indicating that no steady state has been reached between the first two breaths of decreased ventilation), to adjust the duration $T_{IRP'}$ of the IRP of the third breath B2''' to make the level of CO2 expired during the third breath correspond to that expired during the second breath B2" (or the first breath B2'). For example, the IRP of the third breath could be shortened in relation to the IRP of the second breath if the level of expired CO2 is higher during the second breath B2" than during the first breath B2'. This way of dynamically altering the duration of IRPs based on measured CO2 content in expiration gases may ensure that a steady state of expired CO2 is reached within phases of decreased ventilation, or that a more constant steady-state level is reached, and so provide for an even more reliable determination of hemodynamic parameters.

It should be noted that an additional effect of ventilating a patient using the proposed ventilation pattern incorporating inspiratory IRPs at intermediate pressure levels is that a new type of pulmonary stress index is made available at the bedside. This is because the compliance of the respiratory system of the ventilated patient may be determined for two distinct parts of a single inspiration phase, namely a first part of inspiration taking place prior to initiation of the IRP and a second part of inspiration taking place after the IRP. In this way, it can be determined whether the respiratory system compliance increases or decreases during the course of inspiration. This determination may, in accordance with known principles of stress index analysis, be used in the assessment of pulmonary stress.

The invention claimed is:

1. A method for changing effective ventilation of a mechanically ventilated subject, comprising a step of:
   ventilating the subject using a ventilation pattern comprising at least one phase of increased ventilation and at least one phase of decreased ventilation, wherein the phase of decreased ventilation comprises at least one prolonged breath including a respiratory pause (IRP); and
   initiating the respiratory pause when a lung pressure (Palv) of the subject is greater than a minimum lung pressure and less than a maximum lung pressure of the subject during the prolonged breath.

2. The method of claim 1, wherein the respiratory pause (IRP) is initiated at an intermediate pressure level (PIRP) that is higher than a positive end-expiratory pressure (PEEP) level of a previous breath and lower than an end-inspiratory pressure level of the prolonged breath.

3. The method of claim 2, wherein the intermediate pressure level (PIRP) substantially corresponds to a mean lung pressure of the subject during breaths of increased ventilation.

4. The method of claim 1, wherein the respiratory pause (IRP) is an intra-inspiratory pause of an inspiration phase of the prolonged breath.

5. The method of claim 1, wherein the phase of decreased ventilation includes a second breath following the prolonged breath, a respiratory pause of the second breath initiated when the lung pressure (Palv) of the subject is between a minimum lung pressure and a maximum lung pressure of the subject during the second breath, wherein a duration (TIRP") of the respiratory pause of the second breath is shorter than a duration (TIRP') of the respiratory pause of the prolonged breath in order to cause a level of expired CO2 to assume a substantially steady state within the phase of decreased ventilation.

6. The method of claim 1, further comprising
   non-invasively determining a hemodynamic parameter related to the hemodynamics of the subject based on a flow measurement and a CO2 measurement obtained during ventilation of the subject using the ventilation pattern.

7. The method of claim 6, wherein the hemodynamic parameter is determined using a CO2-based Fick technique.

8. A non-transitory computer-readable storage medium including a set of instructions executable via a control computer of a breathing apparatus to change an effective ventilation of a subject connected to the breathing apparatus, the set of instructions, when executed by the control computer of the breathing apparatus, causing the breathing apparatus to ventilate the subject using a ventilation pattern comprising at least one phase of increased ventilation and at least one phase of decreased ventilation, wherein the phase of decreased ventilation comprises at least one prolonged breath including a respiratory pause (IRP), and wherein the breathing apparatus causes the respiratory pause to be initiated when a lung pressure (Palv) of the subject is greater than a minimum lung pressure and less than a maximum lung pressure of the subject during the prolonged breath.

9. A breathing apparatus for changing effective ventilation of a subject connected to the breathing apparatus, comprising:
   a control computer configured to control the operation of the breathing apparatus such that the subject is ventilated using a ventilation pattern comprising at least one phase of increased ventilation and at least one phase of decreased ventilation, wherein the phase of decreased ventilation comprises at least one prolonged breath including a respiratory pause (IRP), and wherein the control computer is configured to cause the respiratory pause to be initiated when a lung pressure (Palv) of the subject is greater than a minimum lung pressure and less than a maximum lung pressure of the subject during the prolonged breath.

10. The breathing apparatus of claim 9, wherein the control computer is configured to cause the respiratory pause (IRP) to be initiated at an intermediate pressure level (PIRP) that is higher than a positive end-expiratory pressure (PEEP) level of a previous breath and lower than an end-inspiratory pressure level of the prolonged breath.

11. The breathing apparatus of claim 10, wherein the intermediate pressure level (PIRP) substantially corresponds to a mean lung pressure of the subject during breaths of increased ventilation.

12. The breathing apparatus of claim 9, wherein the respiratory pause (IRP) is an intra-inspiratory pause of an inspiration phase of the prolonged breath.

13. The breathing apparatus of claim 9, wherein the control computer is configured to cause the phase of decreased ventilation to comprise a second breath following the prolonged breath, a respiratory pause of the second breath initiated when the lung pressure (Palv) of the subject is between a minimum lung pressure and a maximum lung pressure of the subject during the second breath, wherein a duration (TIRP") of the respiratory pause of the second breath is shorter than a duration (TIRP') of the respiratory pause of the prolonged breath in order to cause a level of expired CO2 to assume a substantially steady state within the phase of decreased ventilation.

14. The breathing apparatus of claim 9, further comprising:
    at least one flow sensor measuring at least an expiratory flow of expiration gas exhaled by the subject; and
    at least one CO2 sensor measuring the CO2 content of at least the expiration gas exhaled by the subject,
    wherein the control computer is configured to non-invasively determine a hemodynamic parameter related to the hemodynamics of the ventilated subject based on a flow measurement and a CO2 measurement obtained during ventilation of the subject using the ventilation pattern.

15. The breathing apparatus of claim 14, wherein the hemodynamic parameter is determined using a CO2-based Fick technique.

* * * * *